(12) United States Patent  (10) Patent No.: US 8,784,486 B2
Schuessler  (45) Date of Patent: Jul. 22, 2014

(54) BREAST IMPLANTS HAVING A FLUSH PATCH AND METHODS OF USING SAME TO AUGMENT OR RECONSTRUCT A BREAST

(71) Applicant: Allergan, Inc., Irvine, CA (US)

(72) Inventor: David J. Schuessler, Ventura, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/742,254

(22) Filed: Jan. 15, 2013

(65) Prior Publication Data

US 2013/0131800 A1  May 23, 2013

Related U.S. Application Data

(60) Division of application No. 12/768,500, filed on Apr. 27, 2010, now Pat. No. 8,377,128, which is a continuation-in-part of application No. 12/431,070, filed on Apr. 28, 2009, now Pat. No. 8,070,809.

(60) Provisional application No. 61/038,919, filed on Apr. 28, 2008.

(51) Int. Cl.
   *A61F 2/12*   (2006.01)
(52) U.S. Cl.
   USPC ............................................................ 623/8
(58) Field of Classification Search
   CPC ........................................................ A61F 2/12
   USPC ......................................................... 623/7–8
   See application file for complete search history.

(56) References Cited

U.S. PATENT DOCUMENTS

| | | | |
|---|---|---|---|
| 3,301,251 A | | 1/1967 | Schickedanz |
| 3,852,832 A | | 12/1974 | McGhan |
| 4,605,412 A | | 8/1986 | LaForest et al. |
| 4,636,213 A | | 1/1987 | Pakiam |
| 4,773,909 A | | 9/1988 | Chaglassian |
| 5,019,101 A | | 5/1991 | Purkait et al. |
| 5,022,942 A | | 6/1991 | Yan et al. |
| 5,084,061 A | | 1/1992 | Gau et al. |
| 5,171,269 A | * | 12/1992 | Bark ................................. 623/8 |
| 5,447,535 A | | 9/1995 | Muller |
| 5,456,716 A | | 10/1995 | Iversen |
| 5,480,430 A | * | 1/1996 | Carlisle et al. ..................... 623/8 |
| 5,674,285 A | | 10/1997 | Quaid |
| 5,895,423 A | | 4/1999 | Becker et al. |
| 6,074,421 A | | 6/2000 | Murphy |
| 6,214,045 B1 | * | 4/2001 | Corbitt et al. ..................... 623/8 |
| 6,228,116 B1 | | 5/2001 | Ledergerber |
| 6,602,452 B2 | | 8/2003 | Schuessler |
| 6,692,527 B1 | | 2/2004 | Bellin et al. |
| 6,733,512 B2 | | 5/2004 | McGhan |
| 6,743,254 B2 | * | 6/2004 | Guest et al. ....................... 623/8 |
| 6,955,690 B1 | | 10/2005 | Cao |
| 8,070,809 B2 | | 12/2011 | Schuessler |
| 2003/0149481 A1 | | 8/2003 | Guest |
| 2003/0171768 A1 | | 9/2003 | McGhan |
| 2007/0198085 A1 | | 8/2007 | Benslimane |

(Continued)

FOREIGN PATENT DOCUMENTS

WO  2010022130  2/2010

*Primary Examiner* — Suzette J Gherbi
(74) *Attorney, Agent, or Firm* — Linda Fox

(57) ABSTRACT

Elastomeric fluid-filled prosthetic implants having an elastomeric shell and a flush patch are provided as well as methods for making and using such implants.

14 Claims, 8 Drawing Sheets

(56) References Cited

U.S. PATENT DOCUMENTS

| | | |
|---|---|---|
| 2009/0012372 A1 | 1/2009 | Burnett et al. |
| 2009/0030515 A1 | 1/2009 | Scuessler et al. |
| 2009/0198332 A1 | 8/2009 | Becker |
| 2009/0198333 A1 | 8/2009 | Becker |
| 2009/0202608 A1 | 8/2009 | Alessi et al. |
| 2009/0270985 A1 | 10/2009 | Schuessler |
| 2009/0275974 A1 | 11/2009 | Marchand et al. |
| 2010/0070042 A1 | 3/2010 | Bryan et al. |
| 2010/0168853 A1 | 7/2010 | Job |
| 2012/0197393 A1 | 8/2012 | Yu |
| 2012/0303120 A1* | 11/2012 | Schuessler ......... 623/8 |
| 2013/0304207 A1* | 11/2013 | Schuessler ......... 623/8 |

* cited by examiner

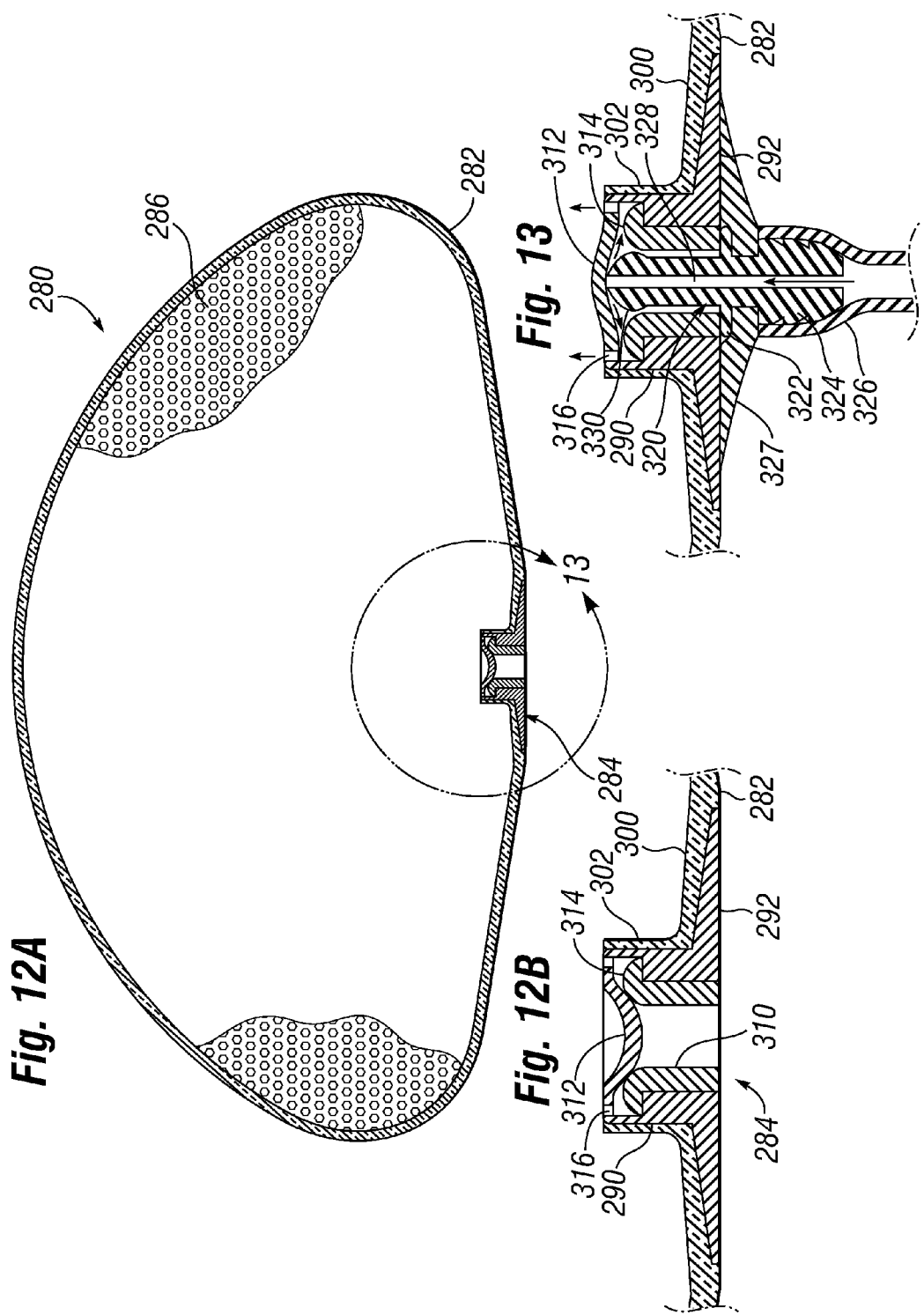

BREAST IMPLANTS HAVING A FLUSH PATCH AND METHODS OF USING SAME TO AUGMENT OR RECONSTRUCT A BREAST

RELATED APPLICATIONS

This application is a divisional of U.S. patent application Ser. No. 12/768,500, filed on Apr. 27, 2010, which is a continuation-in-part of U.S. patent application Ser. No. 12/431,070, filed Apr. 28, 2009, now U.S. Pat. No. 8,070,809, issued on Dec. 6, 2011, and which claims the benefit of U.S. Provisional Patent Application No. 61/038,919 filed Apr. 28, 2008, the entire disclosure of each of these documents being incorporated herein by this reference.

FIELD OF THE INVENTION

The present invention relates to patches for elastomeric implants and, more particularly, to devices and methods for forming a patch flush with an elastomeric implant shell, and methods for augmenting or reconstructing a breast with an implant having a flush patch.

BACKGROUND OF THE INVENTION

Implantable prostheses are commonly used to replace or augment body tissue. In the case of breast cancer, it is sometimes necessary to remove some or all of the mammary gland and surrounding tissue that creates a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various areas of the body, such as the buttocks, chin, calf, etc.

Soft implantable prostheses typically include a relatively thin and quite flexible envelope or shell made of vulcanized (cured) silicone elastomer. The shell is filled either with a silicone gel or with a normal saline solution. The filling of the shell takes place before or after the shell is inserted through an incision.

One process for forming flexible implant shells for implantable prostheses and tissue expanders involves dipping a suitably shaped mandrel into a silicone elastomer dispersion. The outer silicone elastomer shell may have an anatomical configuration, in this case matching the breast, and comes off the mandrel with a shell hole. A patch over the shell hole typically includes an uncured portion directly over the hole and a cured portion covering that and adhered to the inner surface of the shell. The patch is cured and then the hollow interior of the shell is filled with an appropriate gel via a needle hole in the patch. The needle hole in the patch is then sealed with a silicone adhesive and the implant oven cured to achieve cross-linking of the gel.

Another process for forming implant shells is rotational molding, such as the system and methods described in U.S. Pat. No. 6,602,452 to Schuessler. The process also results in a flexible implant shell having a hole that requires a patch.

Patches for flexible implant shells are sized larger than the manufacturing hole to provide some bonding area. The overlap of the patch on the shell results in a slight surface step on the inside or outside of the shell which may be noticeable in the finished product, which is undesirable. Also, such a palpable step or discontinuity may irritate tissue in contact with the exterior of the implant.

Despite many advances in the construction of soft prosthetic implant shells, there remains a need for a smoother joint between a patch and a manufacturing hole in the implant shell.

SUMMARY OF THE INVENTION

In accordance with the present application, a hollow medical implant comprises an elastomeric hollow shell having a contiguous and consistent wall except in an access region, and a patch extending thereacross. The patch is securely bonded to the shell and a peripheral edge of the patch and the shell cooperate to form a flush interface with no surface steps on both interior and exterior surfaces of the implant. In a preferred embodiment, the patch includes a self-sealing channel therein.

In one form, the implant is for implantation in the breast and the elastomeric hollow shell is accordingly shaped. Other implant applications include for the buttocks, testes, calf, etc.

Another embodiment of the present application is a hollow breast implant, including an elastomeric hollow shell shaped for use as breast implant and having a contiguous and consistent wall except in an access region. A patch extends across the access region of the shell and securely bonds thereto. A peripheral edge of the patch and the shell cooperate to form a flush interface with no surface steps on both interior and exterior surfaces of the implant, and the patch including a fluid fill valve therein.

In the aforementioned embodiments, both the elastomeric hollow shell and patch may be made of materials with similar elastic modulus, durometer and elongation, and may even be made of the same material. Desirably, the elastomeric hollow shell is made of a solvent-based solid elastomer and the patch is made of a liquid silicone rubber without a solvent.

In one embodiment, the patch includes a stem projecting radially inward into the interior of the hollow shell and an outer flange extending circumferentially outward from the stem, wherein the shell wall forms a flush butt joint against a peripheral edge of the flange and overlaps an inner surface of the flange and extends at least to the stem. The self-sealing channel may comprise a fluid valve with a valve seat fixed within a lumen of the stem and an elastomeric diaphragm in sealing relationship to the valve seat. In another embodiment, the patch is a substantially flat disk shape and the shell wall covers an entire inner face of the patch. The patch flange may increase in radial thickness from its periphery toward its center such that the portion of the shell wall that overlaps the inner surface of the flange is thickest adjacent the flange periphery.

In one alternative, the self-sealing channel comprises a pre-formed channel in the patch material that permits passage of an instrument for introduction of fluid into the hollow shell and which self-seals after removal of the instrument.

Another useful aspect of the present application is a method of implantation of a breast implant, comprising the steps of:

providing a breast implant having an elastomeric hollow shell with a contiguous and consistent wall except in an access region, and a patch extending across the access region of the shell and securely bonded thereto, wherein a peripheral edge of the patch and the shell cooperate to form a flush interface with no surface steps on both interior and exterior surfaces of the implant, the patch including a self-sealing channel therein;

preparing the breast implant for surgery;

partially filling the hollow shell with sterile saline by injecting the saline through the patch channel;

inserting the partially filled hollow shell into a cavity formed in breast tissue; and adjusting the size of the inserted breast implant by injecting saline through the patch channel.

The self-sealing channel may comprise a fluid valve with a valve seat fixed within the patch and an elastomeric diaphragm in sealing relationship to the valve seat, and the step of partially filling the hollow shell comprises inserting a hollow fill tube connector into the fluid valve and causing saline to flow through the connector into the hollow shell. In one application of the method, the step of inserting the partially filled hollow shell into the cavity includes rolling or folding the shell so it can be inserted through a small incision. The method may also involve allowing the implant to unfold after insertion of the partially filled hollow shell into the cavity and before the step of adjusting the size of the inserted implant. The step of adjusting the size of the inserted breast implant may include using a syringe to inject saline through the patch channel.

In another aspect, the invention includes a hollow medical implant, comprising an elastomeric hollow shell having a contiguous and consistent wall except in an access region. A patch extends across the access region of the shell and securely affixes thereto. The patch has an outer flange and the shell wall forms an exterior butt joint against a peripheral edge of the flange and overlaps an inner surface of the flange in a manner that results in no surface steps.

The present invention also embodies a method of formation of a medical implant, comprising:

a. providing a mold cavity having a sprue orifice;

b. covering the sprue orifice with a patch;

c. introducing a silicone elastomer into the mold cavity;

d. causing the silicone elastomer to distribute generally evenly around the mold cavity and over at least a portion of the patch;

e. curing the silicone elastomer to form a hollow implant shell having the patch bonded thereto; and f. removing the implant shell from the mold cavity.

The patch may be shaped relative to and positioned within the mold cavity so that after formation of the hollow implant shell a peripheral edge of the patch and the shell cooperate to form a flush interface with no sudden surface steps on both interior and exterior surfaces of the implant. The step of introducing preferably includes introducing the silicone elastomer into the mold cavity through the patch. During the step of causing the silicone elastomer to distribute generally evenly around the mold cavity the method may include extending a vent tube through the patch and venting gas from within the mold cavity though the vent tube. Also, a tube may be inserted through the patch for filling the mold cavity with a silicone gel through the tube, which is then cured to form a solid prosthesis.

BRIEF DESCRIPTION OF THE DRAWINGS

Features and advantages of the present invention will become appreciated as the same become better understood with reference to the specification, claims, and appended drawings wherein:

FIG. 12A is a cross-sectional view through an alternative fluid-filled breast implant prosthesis having a molded-in-place flush patch including an alternative self-sealing channel for fluid introduction to the prosthesis;

FIG. 12B is a detailed view of the interface between the flush patch and the shell of the breast implant prosthesis of FIG. 12A;

FIG. 13 is a detailed view similar to FIG. 12B showing insertion of a hollow fill tube connector into a tubular valve seat in the flush patch.

DETAILED DESCRIPTION OF THE PREFERRED EMBODIMENTS

The present invention provides a gel-filled implant prosthesis incorporating a shell composed partly or entirely of a fluid barrier layer, preferably a silicone elastomer. The implant shells of the present invention may have a single material layer of homogeneous or uniform composition, or a laminated or layered configuration. The primary application for gel-filled soft implants is to reconstruct or augment the female breast. Other potential applications are implants for the buttocks, testes, or calf, among other areas. Moreover, though the present invention is particularly advantageous for gel-filled implants, saline filled breast implants or intragastric balloons may be modified to incorporate the benefits herein. Further, tissue expanders which may not be viewed as implants, per se, may also use the concepts disclosed herein. For that matter, the term implant as used herein refers to long and short-term implanted devices.

The implant shells of the present invention are desirably formed using a rotational molding system, such as disclosed in U.S. Pat. No. 6,602,452 to Schuessler, which is expressly incorporated herein by reference. Schuessler discloses a rotational molding machine for forming medical articles, in particular for molding silicone elastomer shells for breast implants. Molding machines other than those that rotate the mold, such as insert molding machines in general (the insert being the patch), may conceivably be used to mold in place the flush patch as described herein, and the advantages of the present invention may even be incorporated into traditional dip molding method, though modifications to the typical dipping mandrel and rod are necessary and will not be described herein.

The advantage of insert molding the patch in place within the shell is that the patch integrates with the shell. That is, the shell material flows over and around the patch and bonds tightly thereto, if not actually melding together to blur any distinct boundaries between the two items. How much of this integration occurs depends on the similarity in the materials, and the mold process parameters such as time and temperature. Preferably the shell comprises a solvent-based solid elastomer (e.g., silicone) and the patch is formed of a liquid silicone rubber (LSR) without a solvent and with a similar elastic modulus, durometer and elongation as the shell. Similar physical properties permit the patch to deform and stretch with the shell which reduces stress concentrators. Alternatively, the materials of the patch and shell could be identical.

Figure 1:
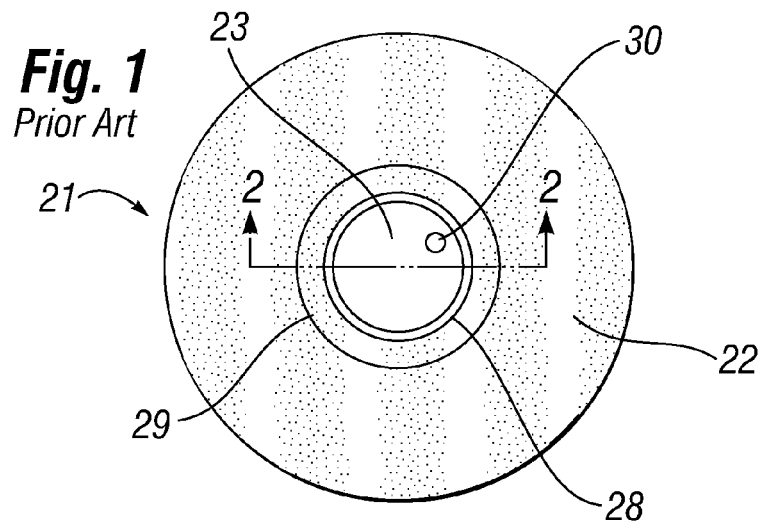
FIG. 1 is a plan view from above of a elastomeric implant sealed by a patch construction in accordance with the prior art.
Figure 2:
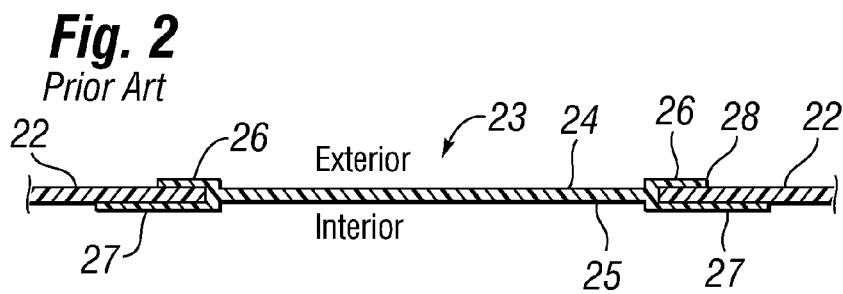
FIG. 2 is a cross-section, to a slightly enlarged scale, when viewed on section line 2-2 of the FIG. 1.

FIGS. 1 and 2 of the drawings illustrate a flexible implant construction of the prior art. A breast prosthesis 21 comprises a textured envelope or shell 22 formed by a conventional molding process on a mandrel. A patch 23 covers an aperture in the shell 22 formed during the mold process. As best seen in FIG. 2, the patch 23 comprises an external overlay 24 and an internal underlay 25, with respective overlapping portions 26, 27, so as to form a sandwich structure. The overlapping sections of the patch 23 and shell 22 as well as those portions of the overlay 24 and underlay 25 which are in contact are bonded together.

The patch can be bonded to the shell by a variety of means including chemical welding or bonding, ultrasonic welding, and heat/pressure fusing. One disadvantage of this process is that a ridge 28 is formed on the exterior as well as a concentric ring 29 formed by the bonding process, part or all of which may be smooth, i.e. where the textured exterior surface area of the shell 22 may be reduced by the overlap of the overlay 24. This is undesirable, because the exterior textured surface area ought to be maximized for surgical reasons. Moreover, the circular ring 29 and peripheral ridge 28 form a ridge on the breast prosthesis 21 that is discernible by feel after implantation. The peripheral portion 27 of the underlay 25 also presents a small internal ridge which is palpable after implantation. These physical discontinuities not only present unnatural tactile sensations, but may result in undesirable chafing between the prosthesis 21 and the breast cavity.

Figure 3:
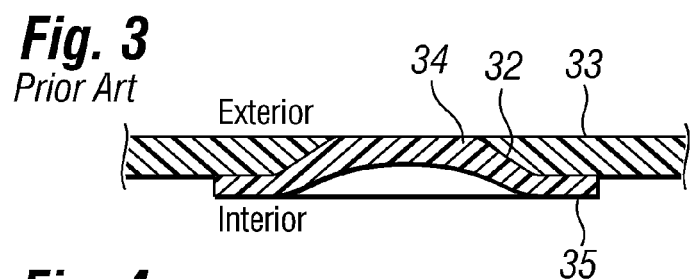
FIG. 3 shows, in cross-section, an alternative patch construction in accordance with the prior art with a chamfered edge of the aperture to be sealed by the patch.

FIG. 3 illustrates an implant shell 33 of the prior art having a chamfered edge 32 around the mold aperture and opening toward the interior of the shell. A patch member 34 bonded to the interior of the shell 33 includes a conical portion which fits closely against the chamfered edge 32 and a peripheral skirt 35 that abuts the interior of the shell 33. This construction eliminates an external ridge, such as at 28 in FIG. 2, but the peripheral skirt 35 still presents an interior ridge.

Figure 4:
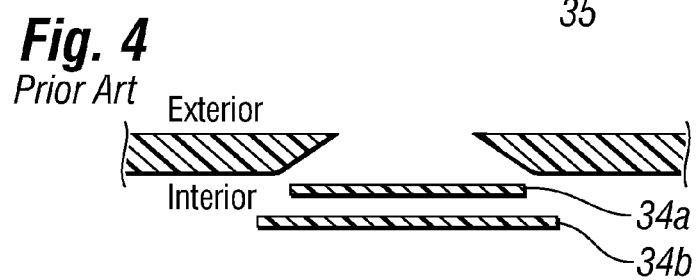
FIG. 4 shows, in cross-section, an alternative patch construction in accordance with the prior art.

Alternatively, as shown in FIG. 4, a patch applied from the interior of the shell 33 in FIG. 3 may comprise two parts, a cap plug portion 34a, slightly larger than the aperture, and an underlay portion 34b, larger still, such that when bonded together, the whole patch extends radially around the aperture in the same manner illustrated in FIG. 3.

The configurations shown in FIGS. 3 and 4 have the advantage that a stronger bond is formed between the edge of the aperture and the patch, since the edge area is increased by virtue of the chamfer 32, when compared to a squared edge, and that no ridge is formed on the exterior at the joint between the patch and the shell. However, as mentioned above, an interior ridge remains. It will be appreciated that the presence of any detectable seam between the patch and the shell represents a stress point which could possibly fail giving rise to leakage of fluid from the prosthesis, which must be avoided.

Figure 5:
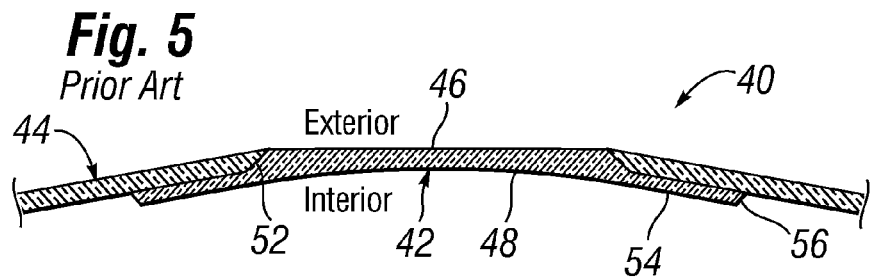
FIG. 5 shows, in cross-section, a still further alternative patch construction in accordance with the prior art.

Finally, FIG. 5 illustrates another patch configuration of the prior art in which a prosthesis 40 includes a patch 42 closing a mold aperture of a shell 44. The patch 42 comprises an external surface 46 visible through the aperture, and an internal surface 48. The aperture has a chamfered mouth 52 to which a peripheral extent of the external surface 46 conforms. The internal surface 48 extends outward from the mouth 52 in a skirt 54 that terminates at a peripheral edge 56. This patch configuration once again presents a smooth external surface to the prosthesis 40, with no ridge, and is somewhat more streamlined than earlier versions, but the internal peripheral edge 56 remains. Again, the edge 56 presents a relatively sudden surface step and stress point around the patch 42 that is discernible from outside the patient after implantation. In this context, a surface step is a relatively sudden surface change such as an increase or decrease in thickness at the shell wall/patch boundary. Another way to define a surface step is a junction between the shell wall and patch that exhibits a step, as opposed to forming a continuous surface tangential to the outer surface of the prosthesis at that location.

Figure 6:
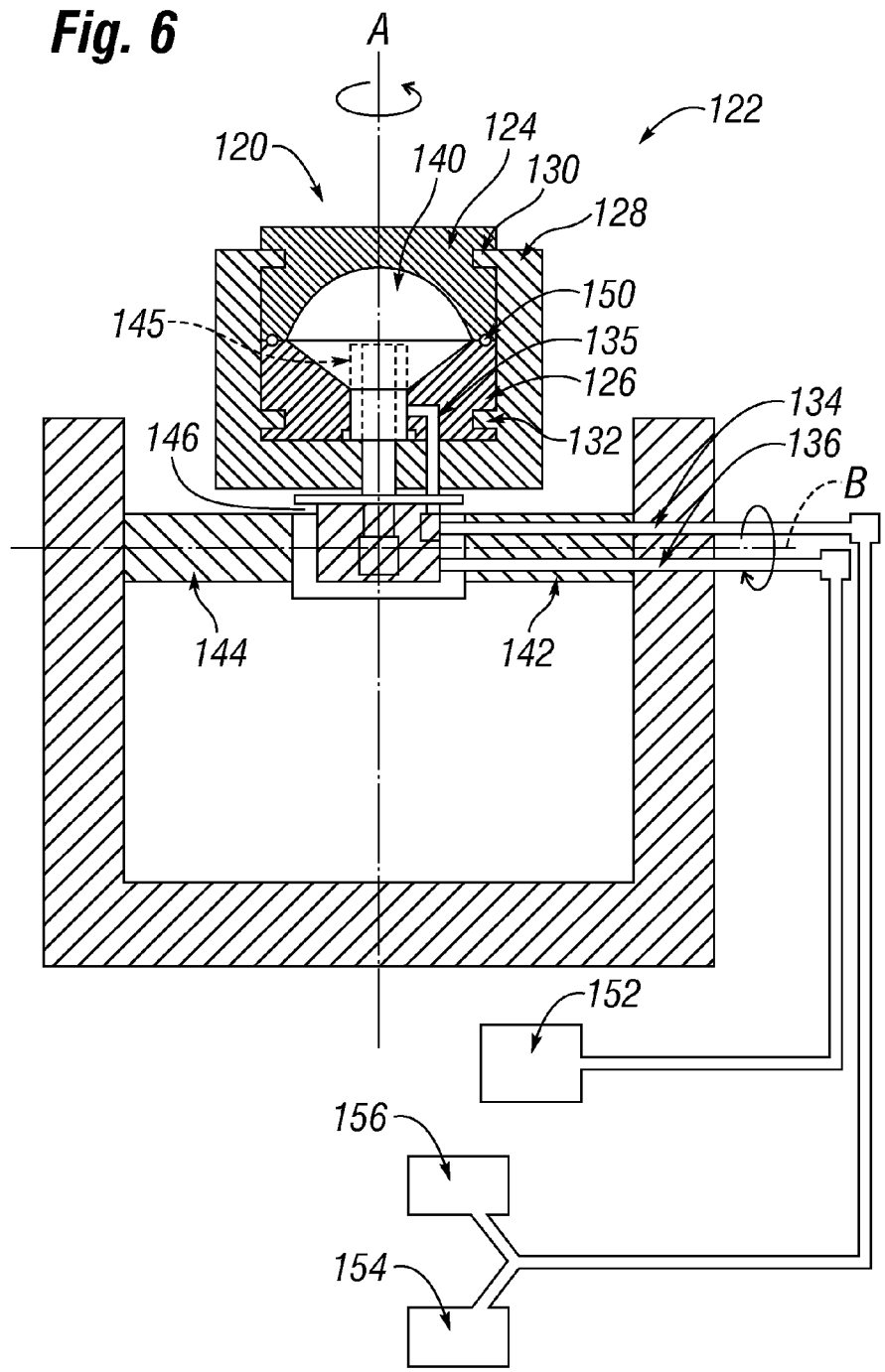
FIG. 6 is a schematic cross-section of an exemplary rotational molding system for use in forming the shell of a soft prosthetic implant of the present invention.

FIG. 6 is a schematic of an embodiment of a rotational molding system similar to that disclosed in Schuessler, U.S. Pat. No. 6,602,452, which can be used to form implant shells of the present invention. A two-piece case mold 120 affixes to a multi-axis rotational mold machine 122 by clamps securing top mold piece 124 and bottom mold piece 126 to clamp base 128 at top locking groove 130 and bottom locking groove 132, respectively. Vacuum connection 134 runs through one arm of the mold machine 122 to a vacuum opening 135. Material connection tube 136, through which silicone elastomer, liner materials, and/or air are injected into the mold cavity 140, may run through or along the same arm 142 as the vacuum connection 134 or by means of another arm 144. The input fluid then continues through a circular sprue tube 145 fitted in a circular opening (not numbered) of bottom mold piece 126. The sprue tube 145 defines a hollow bore that allows materials to enter an internal cavity of the two-piece case mold 120.

The hub 146 of the two arms rotates about axis A in the horizontal direction, while the arms 142, 144 rotate about axis B, which may be perpendicular to axis A. This allows a liner material or silicone elastomer material to uniformly coat the surface of the mold cavity 140. Two-piece case mold 120 may be manufactured from copper, aluminum, or other materials. The top mold piece 124 and bottom mold piece 126 fit together at their mating surfaces, seal with an O-ring 150, and then lock into clamp base 128 of multi-axis rotational molding machine 122.

Material reservoir 152 is fluidly coupled to connection tube 136 for providing silicone elastomer, liner material and/or air to cavity 140. Vacuum source 154 and solvent condenser 156 are fluidly coupled to vacuum connection 134. The hollow bore of the sprue tube 145 communicates with an inner vacuum tube (not shown) which in turn is connected to vacuum opening 135 and vacuum connection 134.

The rotational molding system of FIG. 6 has two distinct advantages over earlier methods for forming soft implant shells. First, the system includes a vacuum vent to the mold via a rotating arm of the equipment, which removes the solvent from silicones and other solvent-based or gas-emitting materials. A second advantage of the rotational molding system is that it enables the formation of articles without seams at the mold parting lines by first coating the inside of the mold with a thin layer of molding material such as polyethylene, polypropylene, nylon, fluoropolymer, polyester resin, polyurethane, epoxy or the like to create a mold liner. After the liner is cast, then the raw material, e.g. silicone elastomer, for the desired implant shell is injected into the mold cavity and similarly rotationally cast inside the liner, resulting in a temporary laminated construct. When the mold is disassembled and the construct is removed from the mold, the liner material and the implant are physically separated resulting in the desired article having a seamless configuration.

Figure 7:
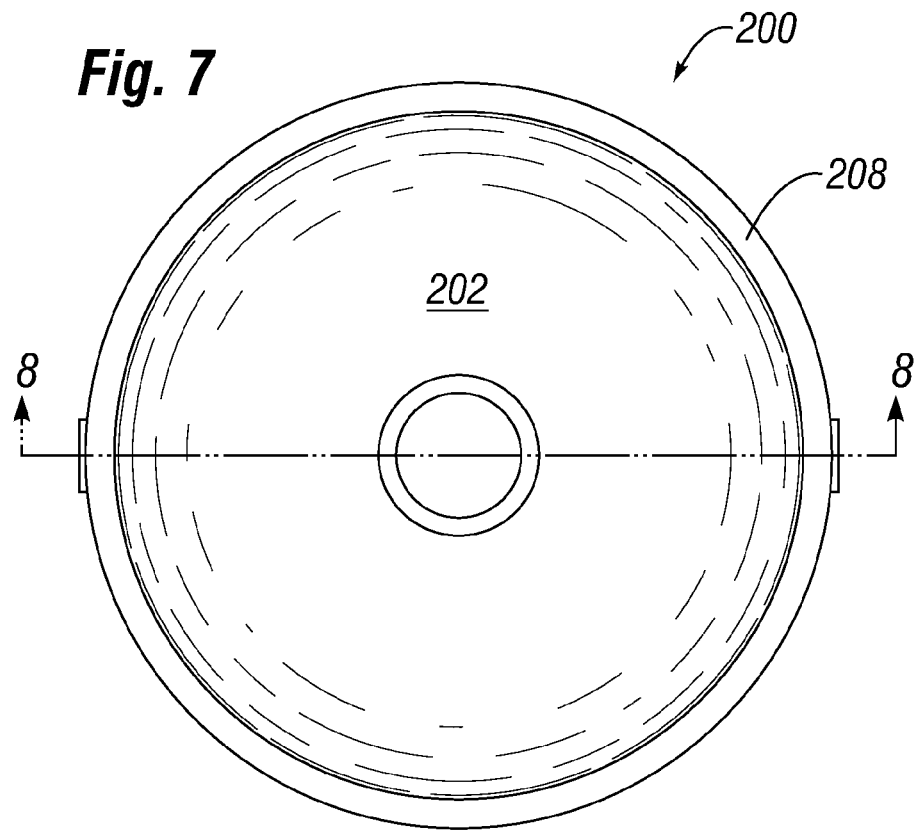
FIGS. 7 and 8 are bottom and sectional views of one embodiment of a mold for use in a rotational molding system such as shown in FIG. 6 to form an elastomeric implant that receives a flush patch of the present invention.
Figure 8:
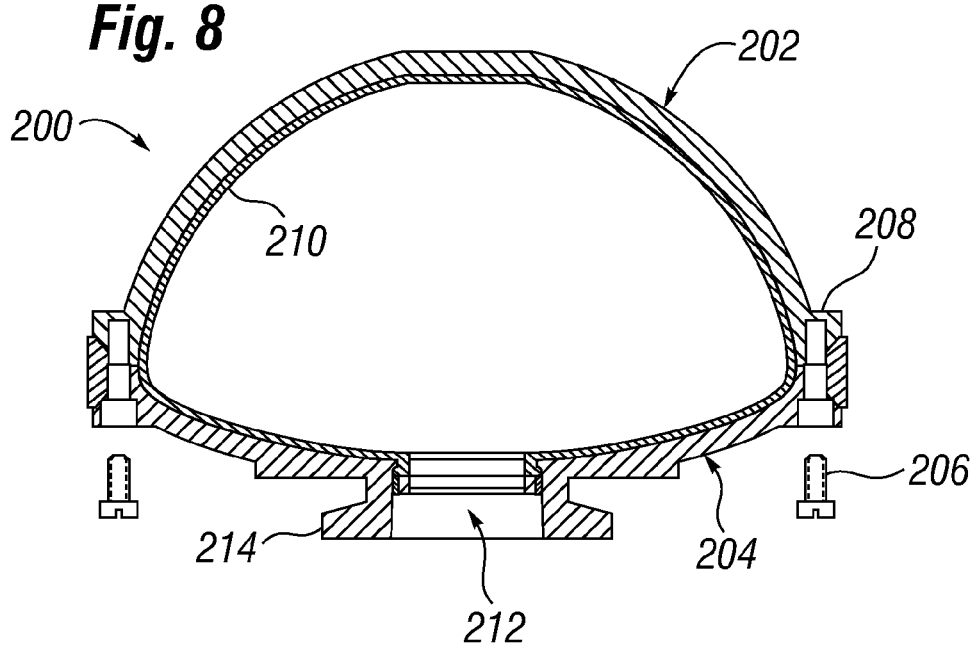

FIGS. 7 and 8 illustrate an alternative mold 200 for a rotational molding system, such as that described with reference to FIG. 6, which can be used to form implant shells of the present invention. As in the earlier embodiment, the mold 200 comprises a top mold piece 202 and bottom mold piece 204 held together by bolts 206 across respective flanges 208. An inner liner 210 is illustrated in cross-section in FIG. 8. Again, the presence of the inner liner 210 is a significant advantage because the implant shells may be formed without a seam that otherwise would result at the intersection of the two mold pieces 202, 204. Desirably, the mold pieces 202, 204 are formed of a metal such as aluminum, and the inner liner 210 is formed of a non-adherent material such as Teflon, for instance ETFE (ethylene-tetrafluoroethylene).

In contrast to the earlier-described embodiment, the inner liner 210 is intended to be reused every time a prosthetic implant shell is formed by the mold. The inner liner 210 remains within the cavity formed by the mold pieces 202, 204, and thus defines the inner surface of the mold 200, during the formation of a number of implants. Preferably the inner liner 210 may remain within the mold pieces 202, 204 for hundreds of uses. As with the earlier-described embodiment, the inner liner 210 is initially formed by rotational molding by injecting free-flowing liner material within the mold pieces 202, 204. The mold 200 functions much like the aforementioned two-piece case mold 120, in that it includes a relatively large circular opening 212 within a lower flange 214 through or into which inserts a sprue tube (such as the sprue tube 145 of FIG. 6).

Figure 9:
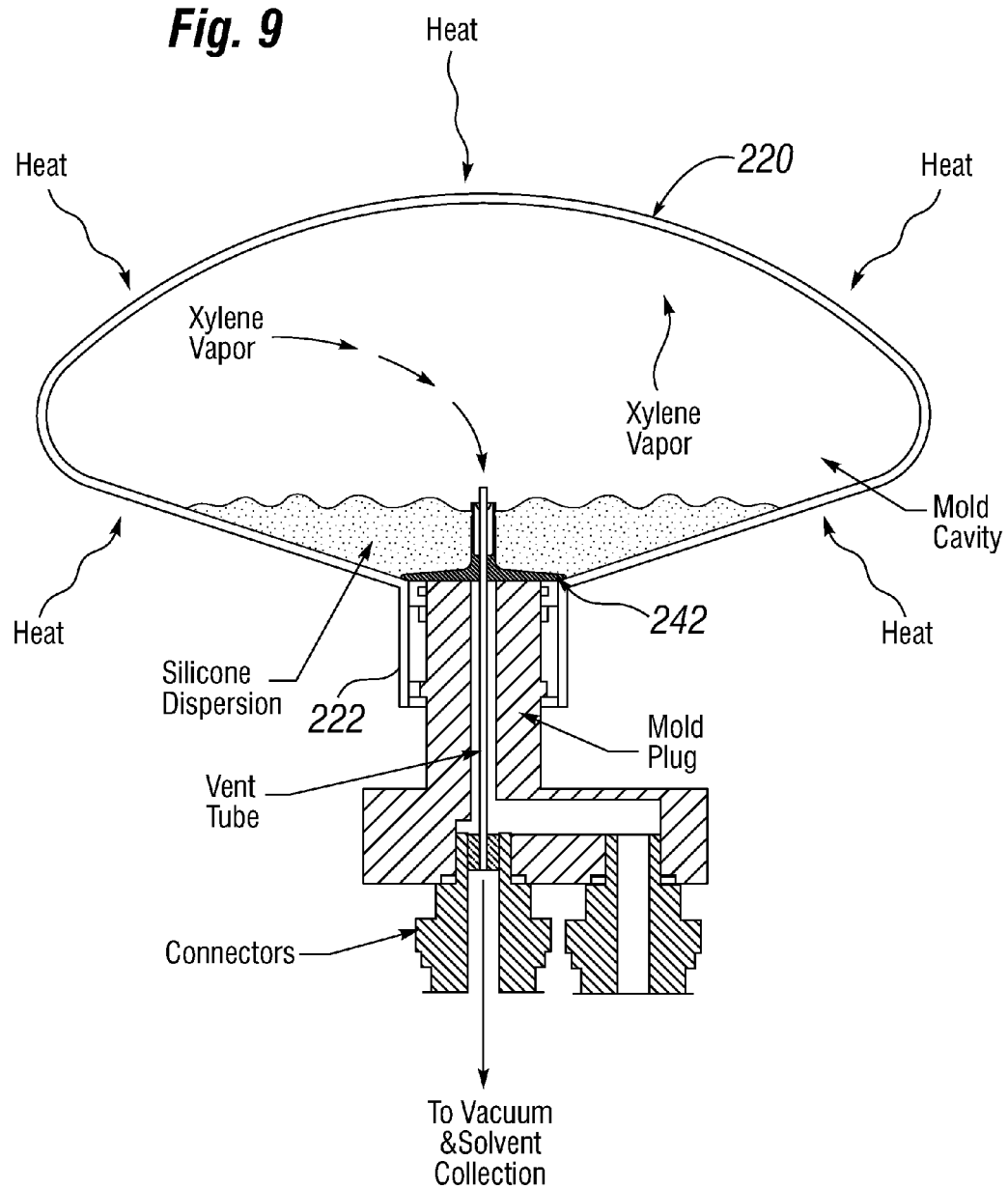
FIG. 9 is a cross-sectional view through an exemplary mold of the present invention showing various elements of a process for forming a flush patch.
Figure 10:
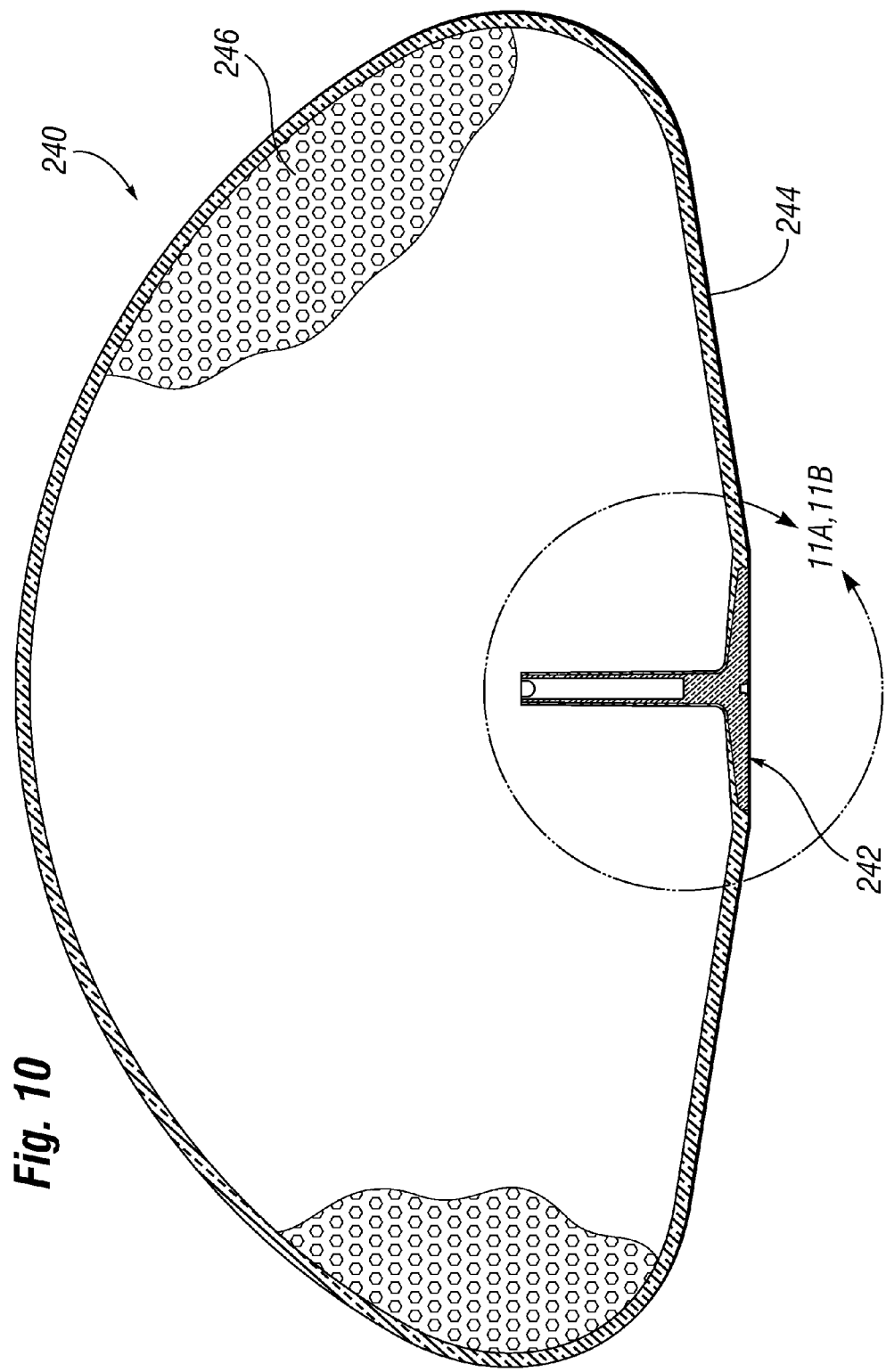
FIG. 10 is a cross-sectional view through an exemplary gel-filled breast implant prosthesis having a molded-in-place flush patch formed in accordance with the present invention.

FIG. 9 schematically illustrates an alternative single-piece mold 220 mounted on a rotational molding machine, such as described above, in the process of forming a soft implant 240 comprising an implant shell 244 having a molded-in patch 242, seen finished in FIG. 10. A single-piece mold 220 obviously eliminates any seam between mold parts, and thus a mold liner is unnecessary. After the implant shell 244 with the molded in-patch 242 is formed, the mold 220 is disengaged from the rotational molding machine leaving the patch visible through a mold neck 222. The resiliency of the material used for the patch and the shell enables them to be folded or otherwise compressed then removed from the mold neck 222.

The molding process involves introducing a silicone dispersion within the mold cavity, rotating the mold 220, and permitting a solvent within the silicone dispersion, such as xylene gas, to be evacuated through a vent tube that extends centrally through the patch 242. The silicone dispersion may be introduced straight into the mold through the patch while holding the patch 242 in place, such as with a spring (not shown), or another channel may be used for inserting the silicone. A mold plug contacts an external surface of the patch 242 and seals within the mold neck 222. The vent tube passes through a bore in the mold plug, and from there to a vacuum and solvent collection system.

FIG. 10 is a cross-sectional view through the exemplary gel-filled breast implant prosthesis 240 comprising the shell 244 and molded-in-place patch 242. The prosthesis 240 may be filled with a gel 246, such as silicone gel.

The patch 242 provides a reinforced access region on the surface of the prosthesis 240 for passage of one or more implements from the exterior to the interior. For instance, the mold process described above desirably utilizes the patch 242 as a reinforced conduit through which both the silicone dispersion tube inserts, as well as the vent tube as shown in FIG. 9. Subsequent to the shell molding process, a third tube may be inserted through the patch to fill the interior of the shell with a silicone gel. And of course a primary function of the patch 242, as detailed herein, is to enable formation of a totally seamless implant with no surface steps inside or out.

Figure 11A:
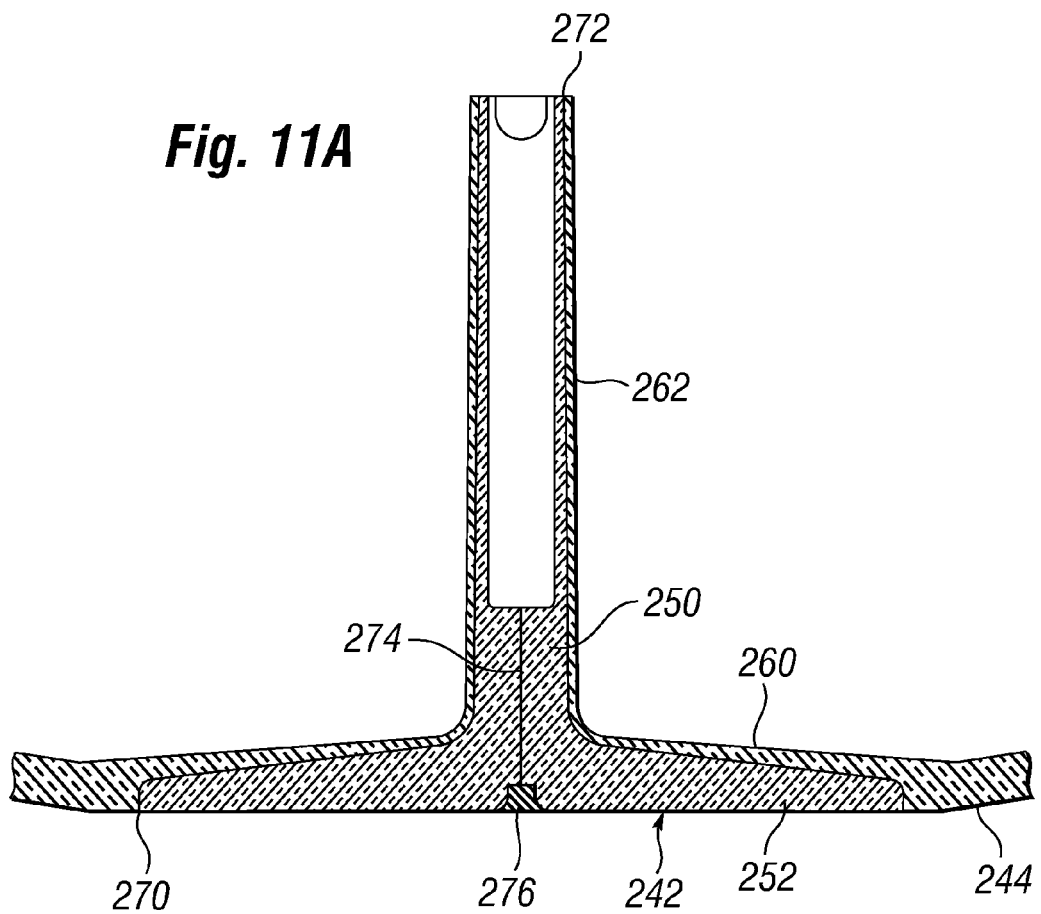
FIG. 11A is a detailed view of the interface between the flush patch and the shell of the breast implant prosthesis of FIG. 10.

FIG. 11A is a detailed view of the interface between the patch 242 and the shell 244. The patch 242 includes a stem 250 projecting directly radially into the interior of the shell 244 and an outward flange 252 generally conforming to and forming a continuation of the exterior shape of the shell 244. The material of the shell 244 extends over the internal surface of the flange 252 at ring 260, extending at least to the stem 250, and preferably continues in a tube 262 around the stem 250. Because the patch flange 252 increases in radial thickness from its periphery toward its center, the wall thickness of the ring 260 tapers thinner from the main part of the shell 244 to the tube 262, and preferably has a uniform thickness along the stem 250. By virtue of the implant material extending therearound, the patch 242 is securely held in place.

By introducing the patch 242 during the process of molding the shell 244, rather than applying the patch to the shell aperture afterwards, the patch integrates with the casting material flowing over and around, thus producing a flush surface both inside and out. In particular, an external surface of the prosthesis including a circular interface line 270 at a flush butt joint between the patch 242 and shell 244 has no ridges or other surface irregularities. A butt joint means the juxtaposition of two edges, in this case an inner-facing edge of the shell 244 and the peripheral edge of the patch 242. The absence of surface interruptions is a great advantage in reducing irritation to tissue surrounding the implanted prosthesis, which has been traumatized and is susceptible to inflammation. Likewise, an internal surface of the prosthesis in the area of the patch 242 has no surface irregularities, and in particular the boundary between the patch 242 and shell 244 is relocated to the radially inner end 272 of the stem 250. There is no surface step at that boundary as the junction between the shell wall and patch forms a continuous surface tangential to the outer surface of the prosthesis at that location. More accurately, by this construction there is no additional surface step added to the existing non-uniformity created by the stem 250. Furthermore, molding the patch 242 into the shell 244 eliminates a secondary manufacturing step of adhering a patch to the shell.

It is important to note that while prior implants utilized a patch to cover an aperture left over as an artifact of the mold process, the shell 244 actually has no such aperture. More accurately, the shell 244 has a contiguous and consistent wall except in an access region across which the patch 242 extends. That is, the access region interrupts the generally constant thickness shell wall. The patch 242 provides an access medium or port through which tubes or other instruments may be inserted into the inner cavity of the shell 244. In the access region, the material of the shell thins to form the ring 260 over the internal surface of the flange 252 and the tube 262 around the stem 250. Because the material of the shell 244 does not cover the open top of the stem 250, an aperture through the shell technically exists, though not the same type of aperture as previously seen with prior art shells. Indeed, in an alternative version in FIG. 11B the shell may not even have an aperture, and the patch in that case does not cover anything but rather parallels, supports, or is juxtaposed against the thinned access region to provide the access port. In this sense, therefore, the term "patch" is sort of a misnomer, but will be retained for the sake of familiarity.

The stem 250 of the patch 242 may be utilized to help prevent clogging of tubes inserted into the cavity of the mold. For example, as seen in FIG. 9, a vent tube extends through a channel 274 (FIG. 11A) in the patch 242 and extends into the mold cavity through the inner end 272 of the stem 250. The silicone dispersion that may at times aggregate near the patch 242 is prevented from entering and potentially clogging the vent tube by virtue of imposition of the upstanding stem 250. The channel 274 also provides an avenue through which a gel-filling tube (not shown) may be introduced after the shell 244 and patch 242 are molded together. For instance, a gel, such as silicone gel 246 shown in FIG. 10, may be injected through a tube inserted through the channel 274. Therefore, the channel 274 may be used for introducing silicone to the mold to form the shell, for venting the mold cavity during the mold process, and/or for introducing the silicone gel into the hollow prosthesis. Instead of providing a pre-formed channel 274, the patch 242 may be made of a material or be configured to be self-sealing. However, given the relatively large bore tubes that may pass through the patch, a channel that is subsequently sealed is more practical. A small well at the opening of the channel 274 that helps guide the vent and gel fill tubes into the channel may be filled with a silicone plug 276, such as a silicone adhesive, to form a completely even outer prosthesis surface.

Figure 11B:
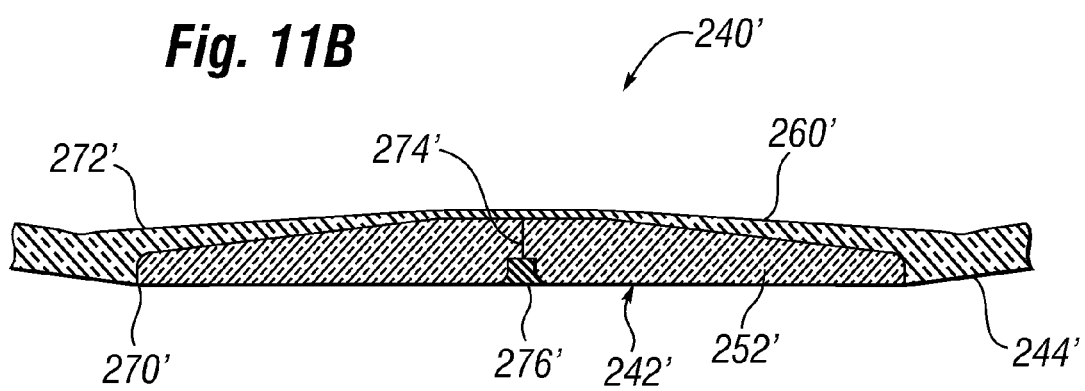
FIG. 11B is a detailed view of the interface between an alternative flush patch and the shell of the breast implant prosthesis of FIG. 10.

FIG. 11B illustrates a portion of a soft implant prosthesis 240' that incorporates a low-profile flush patch 242'. The patch 242' includes an outwardly extending flange 252' but differs from the above-described patch 242 by eliminating the radially extending stem, and instead has a substantially flat disk shape. The patch 242' molds in place so that the surrounding shell 244' again meets flush in a butt joint with the outward flange 252' to form a smooth exterior surface interface 270'. The material of the shell 244' also flows over the inner face of the patch 242' to form a cap 260' that completely eliminates any internal boundary between the patch and shell. The region 272' of the shell 244' adjacent and inward with respect to the outer edge of the patch flange 252' is smooth, and the thickness of the shell 244' at that point entirely covers and cushions any potential tactile discontinuity presented by the edge of the flange. There are certainly no sudden surface steps inside and outside the patch periphery, as in the prior art. A self-closing channel 274' through the patch 242' again provides a passage for insertion of a vent or gel fill tube, and a small plug 276' fills a small well at the outlet of the channel after formation of the implant 240'.

For breast implants, the formed shell is ready for further assembly or processing consistent with the usual manner in creating a final breast implant product. For example, the implant shell is filled with a filler material of silicone gel or other biocompatible gel material well known to those of skill in the art, such as gel 246 shown in FIG. 10.

FIG. 12A is a cross-sectional view through an alternative fluid-filled breast implant prosthesis 280 comprising a shell 282 and molded-in-place patch 284. The prosthesis 280 may be filled with a fluid 286, such as sterile isotonic saline. Much like the patch 242 described above, the patch 284 is desirably molded in place and provides a self-sealing channel through which fluid may be transferred across the wall of the shell 282. Saline-filled implants are known in the art, such as those available from Allergan, Inc. of Irvine, Calif. In particular, the Allergan Natrelle® Collection of breast implants are available with smooth and textured surfaces and varying shapes, to low, moderate and high profile (projection), in a range of volumes. The present application provides saline implants such as the Natrelle® Collection with an improved patch having no surface steps on both interior and exterior surfaces of the implant for a smoother feel. The saline implants of the present application have a silicone rubber shell that is inflated to the desired size with sterile saline intraoperatively, and a self-sealing channel through the shell to provide an adjustable volume implant, providing the potential for further postoperative adjustment.

The patch 284 provides a reinforced access region on the surface of the breast implant 280 for passage of one or more implements from the exterior to the interior. For instance, the mold process described above desirably utilizes the patch 284 as a reinforced conduit through which both the silicone dispersion tube inserts, as well as the vent tube as shown in FIG. 9. Subsequent to the shell molding process, a third tube or nozzle therefore may be inserted through the patch to fill the interior of the shell with sterile saline. The patch 284 enables formation of a totally seamless implant with no surface steps inside or out.

FIG. 12B is a detailed view of the interface between the patch 284 and the shell 282. The patch 284 includes a stem 290 projecting directly radially into the interior of the shell 282 and an outward flange 292 generally conforming to and forming a continuation of the exterior shape of the shell 282. The material of the shell 282 extends over the internal surface of the flange 292 at ring 300, extending at least to the stem 290, and preferably continues in a tube 302 around the stem 290. Because the patch flange 292 increases in radial thickness from its periphery toward its center, the wall thickness of the ring 300 tapers thinner from the main part of the shell 282 to the tube 302, and preferably has a uniform thickness along the stem 290. By virtue of the implant material extending therearound, the patch 284 is securely held in place.

The patch 284 incorporates a self-sealing channel or fluid valve for introduction or removal of fluid such as sterile saline from within the shell 282. The self-sealing channel includes an inner valve seat 310 that cooperates with a valve diaphragm 312. The valve seat 310 comprises a tubular sleeve that fits closely within an inner lumen though the stem 290 of the patch 284. In a preferred embodiment, the diaphragm 312 is integrally molded as an upper end of the stem 290, and the entire element is formed like an inverted cup out of a soft elastomer such as silicone. The diaphragm 312 has a relaxed shape as shown which is concave upward, thus forming a bowl shape. Desirably the valve seat 310 is fixed within the stem 290 with adhesives or the like, though a frictional fit may be adequate. An axially inner end of the valve seat 310 forms a smooth, rounded annulus 314 which may extend radially outward from the main tube of the valve seat so as to rest on a radial step formed on the inner lumen of the stem 290. The rounded annulus 314 provides a smooth surface against which the bowl-shaped valve diaphragm 312 seals. The diaphragm 312 provides a self-sealing valve that is biased by its own resilience against the rounded annulus 314 of the valve seat 310. Two or more small flow passages 316 at the periphery of the diaphragm 312 and outside of the valve seat 310 permit saline flow through the patch 284.

FIG. 13 shows a hollow fill tube connector 320 inserted upward into the tubular valve seat 310. The connector 320 has an outwardly directed flange 322 that limits insertion depth into the valve seat 310, and a barbed outer nipple 324 to which a flexible fill tube 326 may be secured. A strap closure 327 may be used to help secure the connector 320 in place. A central fluid flow lumen 328 passes through the length of the connector 320.

The fill tube connector 320 includes a blunt distal end 330 that pushes up the diaphragm 312 and allows fluid flow thru the small flow passages 316 as shown by the flow arrows. The resiliency and shape of the diaphragm 312 permits it to be deformed upward by the blunt distal end 330, and then spring back into the shape of FIG. 12B when the connector 320 is removed, thus self-sealing against the rounded annulus 314 of the valve seat 312. Alternatively, a self-sealing septum pierced by Huber or non-coring needles may be used to inject or remove saline from the shell 282, or a pre-formed channel as in FIGS. 11A and 11B may be used.

In a preferred implant sequence, the fully formed breast implant prosthesis 280 is removed from its sterile packaging in the surgery room. The medical technician inserts the hollow fill tube connector 320 attached to tubing 326 into the patch valve 284 as a means for fluid transfer to and from the interior of the breast implant 280. The technician compresses the implant 280 (or provides suction) to remove most of the air therein. The implant 280 is then slightly filled with saline, and the residual air within is isolated near the patch valve 284 and expelled manually.

Figure 14:
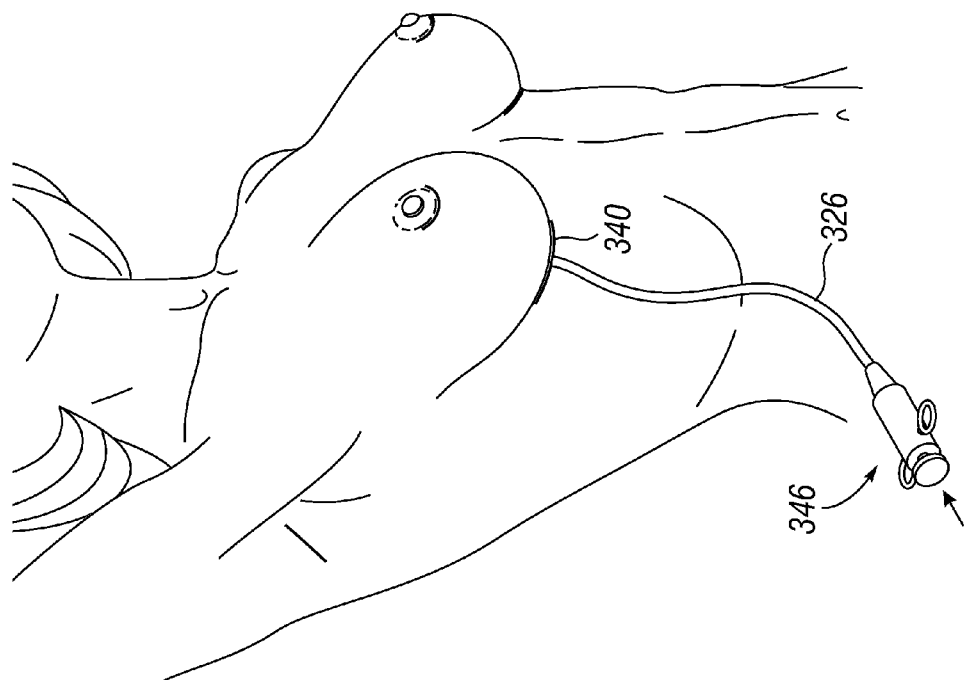
FIGS. 14 and 15 schematically illustrate the torso of a breast implant patient and a procedure for implanting and filling a saline-filled breast implant.
Figure 15:
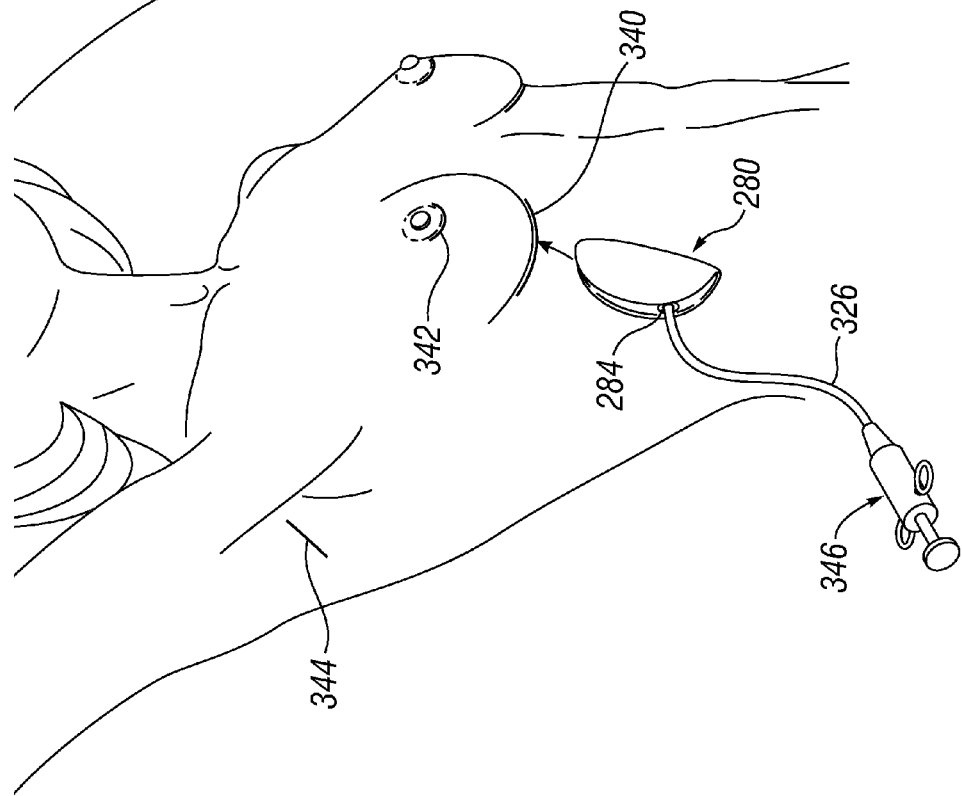

FIGS. 14 and 15 schematically illustrate the torso of a breast implant patient and a procedure for implanting and filling a saline-filled breast implant such as the breast implant 280 of FIG. 12A. Several possible incision locations include an inframammary incision 340 in the fold below the breast, a periareolar incision 342 around the nipple, and a transaxillary incision 344 at the underarm. The surgeon makes an incision in one of these locations, and prepares a pocket within the breast tissue of the approximate size of the implant.

FIG. 14 shows the near-empty implant 280 having been rolled or folded so it can be inserted through a small incision—in this case the inframammary incision 340. The filling tube 326 remains connected, and a fill syringe 346 or other such device attaches to a proximal end thereof.

Once inserted into the pre-formed anatomical pocket, as in FIG. 15, the surgeon allows or causes the implant 280 to unfold. Next, using the syringe 346 the surgeon fills the implant 280 with saline to the desired volume. After ensuring the implant is filled to the proper volume, and checking any asymmetry if this is the second implant inserted, the surgeon removes the fill tube connector 320 from the patch valve 284 by pulling it while bracing the posterior side of the implant. Finally, the surgeon closes the incision 340.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A method of implanting a breast, comprising:
providing a breast implant having an elastomeric hollow shell with a contiguous and consistent wall except in an access region, and a patch extending across the access region of the shell and securely bonded thereto, wherein a peripheral edge of the patch and the shell cooperate to form a flush interface with no surface steps on both interior and exterior surfaces of the implant, the patch including a self-sealing channel therein;
partially filling the hollow shell with sterile saline by injecting the saline through the patch channel;
inserting the partially filled hollow shell into a cavity formed in breast tissue; and
adjusting the size of the inserted breast implant by injecting saline through the patch channel.

2. The method of claim 1, wherein the self-sealing channel comprises a fluid valve with a valve seat fixed within the patch and an elastomeric diaphragm in sealing relationship to the valve seat, and the step of partially filling the hollow shell comprises inserting a hollow fill tube connector into the fluid valve and causing saline to flow through the connector into the hollow shell.

3. The method of claim 1, wherein the step of inserting the partially filled hollow shell into the cavity includes rolling or folding the shell so it can be inserted through a small incision.

4. The method of claim 1, wherein after insertion of the partially filled hollow shell into the cavity, the implant is allowed to unfold before the step of adjusting the size of the inserted implant.

5. The method of claim 1, wherein the step of adjusting the size of the inserted breast implant includes using a syringe to inject saline through the patch channel.

6. A method of reconstructing or augmenting a breast, comprising:
providing a breast implant having an elastomeric hollow shell with a contiguous and consistent wall except in an access region, and a patch extending across the access region of the shell and securely bonded thereto, wherein a peripheral edge of the patch and the shell cooperate to form a flush interface with no surface steps on both interior and exterior surfaces of the implant, wherein the patch includes a stem projecting inward into the interior of the hollow shell and an outer flange extending circumferentially outward from the stem and wherein the shell wall forms a flush butt joint against a peripheral edge of the flange and overlaps an inner surface of the flange and extends at least to the stem;
preparing the breast implant for surgery;
partially filling the hollow shell with sterile saline by injecting the saline through the stem;
inserting the partially filled hollow shell into a cavity formed in breast tissue; and
adjusting the size of the inserted breast implant by injecting saline through the stem.

7. The method of claim 6, wherein both the elastomeric hollow shell and patch are made of materials with similar elastic modulus, durometer and elongation.

8. The method of claim 6, wherein both the elastomeric hollow shell and patch are made of the same material.

9. The method of claim 6, wherein the elastomeric hollow shell is made of a solvent-based solid elastomer and the patch is made of a liquid silicone rubber without a solvent.

10. The method of claim 6, wherein the valve comprises a fluid valve with a valve seat fixed within the patch and an elastomeric diaphragm in sealing relationship to the valve seat.

11. The method of claim 6, wherein the valve comprises a pre-formed channel in the patch material that permits passage of an instrument for introduction of fluid into the hollow shell and which self-seals after removal of the instrument.

12. A method of reconstructing or augmenting a breast, comprising:
providing a breast implant having an elastomeric hollow shell shaped for use as breast implant and having a contiguous and consistent wall except in an access region, and
a patch extending across the access region of the shell and securely bonded thereto, wherein a peripheral edge of the patch and the shell cooperate to form a flush interface with no surface steps on both interior and exterior surfaces of the implant, the patch including a fluid fill valve therein, wherein the fluid fill valve comprises a fluid valve with a valve seat fixed within the patch and an elastomeric diaphragm in sealing relationship to the valve seat, and wherein the fluid fill valve further comprises flow passages at the periphery of the elastomeric diaphragm; and at least partially filling the hollow shell with sterile saline by injecting the saline through the patch channel;

inserting the at least partially filled hollow shell into a cavity formed in breast tissue; and adjusting the size of the inserted breast implant by injecting saline through the patch channel.

13. A method of reconstructing or augmenting a breast, the method comprising:

providing a breast implant, comprising an elastomeric hollow shell shaped for use as breast implant and having a contiguous and consistent wall except in an access region; and a patch extending across the access region of the shell and securely bonded thereto, wherein a peripheral edge of the patch and the shell cooperate to form a flush interface with no surface steps on both interior and exterior surfaces of the implant, the patch including a fluid fill valve therein;

wherein the fluid fill valve comprises a fluid valve with a valve seat fixed within the patch and an elastomeric diaphragm in sealing relationship to the valve seat; and wherein the patch includes a stem projecting into an interior of the hollow shell and the valve seat comprises a tubular sleeve fitted within the stem.

14. The method of claim 13 wherein the fluid fill valve further comprises flow passages at the periphery of the elastomeric diaphragm.

* * * * *